(12) United States Patent
Nakamura et al.

(10) Patent No.: US 10,093,600 B2
(45) Date of Patent: Oct. 9, 2018

(54) METHOD FOR PRODUCING TRIFLUOROETHYLENE

(71) Applicant: Asahi Glass Company, Limited, Chiyoda-ku (JP)

(72) Inventors: Masahiko Nakamura, Chiyoda-ku (JP); Hidekazu Okamoto, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 15/218,115

(22) Filed: Jul. 25, 2016

(65) Prior Publication Data

US 2016/0332937 A1    Nov. 17, 2016

Related U.S. Application Data

(63) Continuation of application No. PCT/JP2015/052531, filed on Jan. 29, 2015.

(30) Foreign Application Priority Data

Jan. 30, 2014  (JP) ................................. 2014-015963

(51) Int. Cl.
C07C 17/25     (2006.01)
B01J 8/24      (2006.01)
C09K 5/04      (2006.01)

(52) U.S. Cl.
CPC ................ C07C 17/25 (2013.01); B01J 8/24 (2013.01); C09K 5/045 (2013.01); C09K 2205/126 (2013.01)

(58) Field of Classification Search
CPC ....................................................... C07C 17/25
See application file for complete search history.

(56) References Cited

U.S. PATENT DOCUMENTS

| | | |
|---|---|---|
| 2005/0020862 A1 | 1/2005 | Tung et al. |
| 2007/0129579 A1 | 6/2007 | Wang et al. |
| 2009/0234165 A1 | 9/2009 | Chiu et al. |
| 2010/0022809 A1 | 1/2010 | Cottrell et al. |
| 2011/0144394 A1 | 6/2011 | Scheidle et al. |
| 2011/0288347 A1 | 11/2011 | Chiu et al. |

(Continued)

FOREIGN PATENT DOCUMENTS

| | | |
|---|---|---|
| JP | 2007-500127 | 1/2007 |
| JP | 2010-533151 | 10/2010 |

(Continued)

OTHER PUBLICATIONS

Guillet, D. et al. WO2011157907A1, Dec. 2011, pp. 1-5; English translation.*

(Continued)

Primary Examiner — Medhanit W Bahta
(74) Attorney, Agent, or Firm — Oblon, McClelland, Maier & Neustadt, L.L.P.

(57) ABSTRACT

A method to efficiently and stably produce trifluoroethylene from 1,1,1,2-tetrafluoroethane is provided. In the method, a material gas containing 1,1,1,2-tetrafluoroethane in a gaseous phase and calcium oxide in a solid phase are brought into contact with each other in a reactor. Clogging of the reactor is less likely to occur, the load of the moisture removal process is light, and problems such as a decrease in the yield of trifluoroethylene do not arise.

11 Claims, 3 Drawing Sheets

(56) References Cited

U.S. PATENT DOCUMENTS

2012/0022302 A1    1/2012  Bektesevic et al.
2012/0301373 A1  11/2012  Chiu et al.
2014/0012049 A1    1/2014  Wang et al.

FOREIGN PATENT DOCUMENTS

| JP | 2013-543510 | 12/2013 | | |
|----|----|----|----|----|
| WO | WO 97/29065 | 8/1997 | | |
| WO | WO 2011/157907 A1 | 12/2011 | | |
| WO | WO 2011157907 A1 * | 12/2011 | ............. | C07C 17/25 |
| WO | WO 2014/178353 A1 | 11/2014 | | |

OTHER PUBLICATIONS

Ljupković, R. B. et al. "Significance of the structural properties of CaO catalyst in the production of biodiesel: An effect on the reduction of greenhouse gas emissions" Hem. ind. 68 (4) 399-412 (2014).*

International Search Report dated Apr. 21, 2015 in PCT/JP2015/052531, filed on Jan. 29, 2015.

* cited by examiner

METHOD FOR PRODUCING TRIFLUOROETHYLENE

This application is a continuation of PCT Application No. PCT/JP2015/052531, filed on Jan. 29, 2015, which is based upon and claims the benefit of priority from Japanese Patent Application No. 2014-015963 filed on Jan. 30, 2014. The contents of those applications are incorporated herein by reference in their entireties.

TECHNICAL FIELD

The present invention relates to a method for producing trifluoroethylene, more particularly, a method for producing trifluoroethylene from 1,1,1,2-tetrafluoroethane as a material.

BACKGROUND ART

Trifluoroethylene (HFO-1123), which has a low global warming potential (GWP), is greatly expected in recent years as a new refrigerant which may replace difluoromethane (HFC-32) and 1,1,1,2,2-pentafluoroethane (HFC-125) which are greenhouse gases.

In this specification, abbreviated names (e.g. refrigerant numbers) of halogenated hydrocarbon compounds are described in brackets after the compound names. As the case requires, the abbreviated names are employed instead of the compound names.

Heretofore, a method for producing such HFO-1123 from 1,1,1,2-tetrafluoroethane (HFC-134a) which is a relatively inexpensive material has been known. For example, Patent Document 1 discloses a method of subjecting HFC-134a to dehydrofluorination using a metal fluoride as a catalyst. Further, Patent Document 2 discloses a method of reacting HFC-134a with a metal hydroxide such as calcium hydroxide.

However, by the method disclosed in Patent Document 1, the degree of conversion of HFC-134a is low.

Further, the method disclosed in Patent Document 2 has the following problems.

(1) Calcium hydroxide has a high adhesion property between particles, and the particles are likely to be solidified to clog a part of the reactor.

(2) In the reaction of calcium hydroxide with HFC-134a, the amount of water formed as a by-product tends to be large, and accordingly a load of moisture removal process tends to be heavy before the obtained HFO-1123 is used as a refrigerant.

(3) When calcium hydroxide is used for the reaction with HFC-134a, side reaction of HFO-1123 with a large amount of water formed as a by-product tends to occur and a carboxylic acid fluoride and a carboxylate are generated, thus decreasing the yield of HFO-1123.

Therefore, for production of HFO-1123 useful as a new refrigerant which replaces greenhouse gases by using HFC-134a which is an inexpensive material, an efficient production method has been desired in which the degree of conversion of HFC-134a and the yield of HFO-1123 are high, clogging of the reactor is less likely to occur and the load of the moisture removal process is light, and problems such as a decrease in the yield of HFO-1123 will not arise.

PRIOR ART DOCUMENTS

Patent Documents

Patent Document 1: JP-A-2010-533151
Patent Document 2: WO2011/157907

DISCLOSURE OF INVENTION

Technical Problem

Under these circumstances, it is an object of the present invention to provide a method for efficiently producing HFO-1123 stably by using HFC-134a which is an inexpensive material, without causing clogging of the reactor, a decrease in the yield of a product, etc., and without significant load to the subsequent process.

Solution to Problem

The method for producing HFO-1123 of the present invention comprises bringing a material gas containing HFC-134a and calcium oxide into contact with other in a reactor.

Advantageous Effects of Invention

According to the present invention, in production of HFO-1123 from HFC-134a which is an inexpensive material, HFO-1123 can be efficiently produced with sufficiently high degree of conversion of 134a and selectivity for HFO-1123, without causing problems such as clogging of the reactor, an increase in the load to the moisture removal process by formation of moisture as a by-product, and a decrease in the yield of HFO-1123.

Further, according to the production method of the present invention, by the after-described reaction, HFC-134a can be reacted with a sufficiently high degree of conversion and HFO-1123 can be obtained with a high selectivity.

Further, the production method of the present invention, in which HFC-134a and calcium oxide are reacted, has the following advantage as compared with a conventional method of reacting HFC-134a with calcium hydroxide.

That is, calcium oxide has lower adhesion property between particles as compared with calcium hydroxide, and the particles are less likely to be solidified, whereby the reactor is less likely to be clogged, and the reactor can be continuously operated stably over a long period of time. Further, risks of accidents such as a sudden pressure increase by clogging of the reactor are reduced. Further, since calcium hydroxide is produced from calcium oxide as a material, calcium oxide is available at a lower cost than calcium hydroxide. Still further, in the above reaction using calcium oxide, the amount of water formed as a by-product can be reduced as compared with a case of using calcium hydroxide, and accordingly the load of the moisture removal process required before the obtained HFO-1123 is used as a refrigerant can be reduced, formation of a carboxylic acid fluoride and a carboxylate in side reaction of HFO-1123 and water can be suppressed, and the yield of HFO-1123 can be increased.

DESCRIPTION OF EMBODIMENTS

Figure 1:
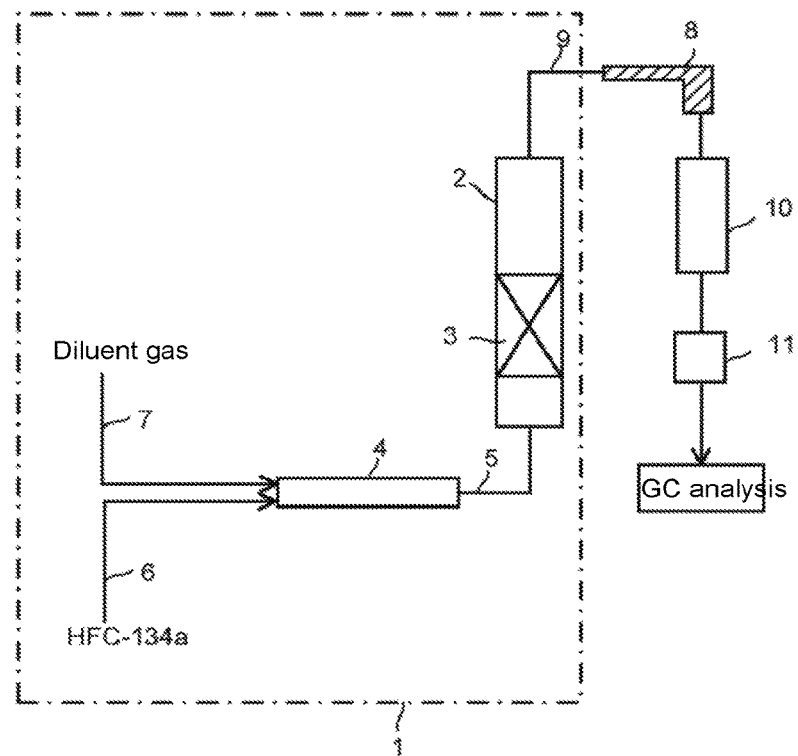
FIG. 1 is a drawing illustrating an example of a fixed bed reaction apparatus used in the production method of the present invention.

Now, an embodiment of the present invention will be described. The present invention is by no means restricted to the following embodiment.

The production method according to an embodiment of the present invention comprises bringing a material gas containing HFC-134a and calcium oxide into contact with each other in a reactor to make dehydrofluorination of HFC-134a progress thereby to produce HFO-1123.

In the production method of the present invention, the reaction of HFC-134a and calcium oxide may be represented by the following reaction formula (1):

$$2CF_3-CH_2F+CaO \rightarrow 2CF_2=CHF+CaF_2+H_2O \quad (1)$$

When HFC-134a is brought into contact with calcium oxide, dehydrofluorination occurs in which one of fluorine atoms bonded to a carbon atom to which three fluorine atoms are bonded between the two carbon atoms of HFC-134a, and one of hydrogen atoms bonded to the other carbon atom, leave simultaneously. And, by such dehydrofluorination of HFC-134a, HFO-1123 forms. On that occasion, hydrogen fluoride formed of the fluorine atom and the hydrogen atom which have left react with calcium oxide to form calcium fluoride and water simultaneously.

The production method of the present invention may be a continuous production method or may be a production method by the batch. In a continuous production method, each of supplies of HFC-134a and calcium oxide as reaction components to the reaction site (for example, a heated reactor) may be carried out continuously, or only supply of one component may be carried out continuously, and the other component is supplied by the batch. In a case where only supply of one component is carried out continuously, it is preferred to supply calcium oxide to the reaction site by the batch and then to continuously supply HFC-134a to the reaction site.

Further, in production by the batch, both the components are supplied by the batch. Either of the supply of HFC-134a and the supply of calcium oxide to the reaction site may be carried out first, or the supplies of both the components may be carried out simultaneously. That is, in a case where either one of HFC-134a and calcium oxide is not supplied to the reactor when the other is supplied, the component to be supplied later is supplied, while the previously supplied component stays in the reactor, and HFC-134a and calcium oxide are brought into contact with each other in the reactor for a predetermined time.

(HFC-134a)

HFC-134a used in the present invention may be HFC-134a with a purity of 100% (mol %), or may be one containing 1,1,2,2-tetrafluoroethane (HFC-134) which is an impurity derived from the production method. In a case where it contains HFC-134, the purity of HFC-134a is preferably at least 50 mol %. That is, the material gas may be one containing HFC-134a with a purity of 100% (mol %) or may be one containing HFC-134a with a purity of at least 50 mol % containing impurities such as HFC-134.

When HFC-134a and calcium oxide are brought into contact with each other, HFC-134a in a gaseous phase may be brought into contact with calcium oxide in a solid phase or a liquid phase, or HFC-134a in a liquid phase may be brought into contact with calcium oxide in a solid phase or a liquid phase. However, if HFC-134a is in a liquid phase, the pressure of the liquid phase tends to be too high and reaction at high temperature is difficult, and thus it is preferred to bring HFC-134a in a gaseous phase is brought into contact.

(Calcium Oxide)

Calcium oxide used in the present invention may be calcium oxide with a purity of 100% (wt %) or may be one containing compounds other than calcium oxide. The compounds other than calcium oxide may, for example, be calcium hydroxide, calcium carbonate, sodium hydroxide and water which are impurities derived from the production method. In a case where calcium oxide contains such impurities, the purity of calcium oxide is preferably at least 50 wt %, most preferably at least 60 wt %.

When HFC-134a and calcium oxide are brought into contact with each other, calcium oxide may be in a solid phase, or may be in a liquid phase having calcium oxide dissolved or dispersed in a liquid medium in which calcium oxide can be dissolved or dispersed. The liquid medium in which calcium oxide is dissolved or dispersed may, for example, be water, an alcohol such as methanol or ethanol, a chlorine solvent such as carbon tetrachloride, N,N-dimethylformamide, N,N-dimethylacetamide, dimethylsulfoxide, tetraethylene glycol dimethyl ether, triethylene glycol dimethyl ether, diethylene glycol dimethyl ether or propylene glycol monomethyl ether monoacetate. In a case where calcium oxide is in a liquid phase as dissolved or dispersed in the liquid medium, the pressure tends to be too high and reaction at high temperature is difficult, and accordingly calcium oxide is preferably in a solid phase.

Now, the method of the present invention will be described with reference to an embodiment in which HFC-134a in a gaseous phase continuously supplied to the reactor is brought into contact with calcium oxide in a solid phase charged by the batch, however, the production method of the present invention is not limited to such an embodiment.

In the embodiment in which calcium oxide in a solid phase is used, the specific surface area of calcium oxide measured by a BET method (BET specific surface area) is preferably from 0.1 to 500 m$^2$/g. When calcium oxide in a solid phase has a BET specific surface area within the above range, it reacts with HFC-134a with a high reaction rate, whereby the reaction efficiency will be favorable, and in addition, the density of the particles is not too low, whereby the particles are less likely to fly and favorable handling efficiency is obtained. The BET specific surface area of calcium oxide is more preferably from 1 to 400 m$^2$/g, further preferably from 50 to 400 m$^2$/g, most preferably from 100 to 200 m$^2$/g.

(Other Component)

In the present invention, in addition to HFC-134a and calcium oxide as reaction components, other components may be contained in each of the gaseous phase and the solid phase.

The component other than HFC-134a in the gaseous phase is not particularly limited, however, with a view to suppressing side reaction, an inert gas such as nitrogen, argon or helium is preferably contained. By such a gas, HFC-134a as a reaction component can be diluted. Hereinafter such a gas will be referred to as a diluent gas.

The content of the diluent gas is preferably from 0 to 95 mol %, particularly preferably from 0 to 50 mol % based on the total amount of components in the gaseous phase containing HFC-134a, in view of the reaction efficiency, suppression of side reaction, etc. And, the content of HFC-134a based on the total amount of the components in the gaseous phase is preferably from 5 to 100 mol %, particularly preferably from 50 to 100 mol %.

In the embodiment in which HFC-134a in a gaseous phase is continuously brought into contact with and reacted with calcium oxide in a solid phase, by controlling the flow rates of the respective components in the gaseous phase containing HFC-134a per unit time, the molar ratio of HFC-134a in the material gas can be controlled.

The components other than calcium oxide in the solid phase is not particularly limited and may, for example, a carrier to support calcium oxide. The carrier may, for example, be an alumina carrier, a zirconia carrier, a silica carrier, a silica-alumina carrier, a carbon carrier represented by activated carbon, a barium sulfate carrier or a calcium carbonate carrier. Activated carbon may, for example, be activated carbon prepared from a material such as wood, charcoal, fruit shell, coconut shell, peat, lignite or coal.

(Reactor and Reaction Conditions)

The reactor in which HFC-134a and calcium oxide are reacted is not particularly limited in terms of the shape and the structure so long as the reactor can withstand the temperature and the pressure in the reactor described hereinafter. The reactor may, for example, be a cylindrical vertical reactor. As the material of the reactor, glass, iron, nickel, or an alloy containing iron or nickel as the main component may, for example, be mentioned. The reactor may have a heating means such as an electric heater to heat the interior of the reactor.

In the embodiment in which HFC-134a in a gaseous phase continuously supplied is brought into contact with calcium oxide in a solid phase charged by the batch in the reactor, calcium oxide charged in the reactor to form a solid phase may be accommodated in the form of either a fixed bed or a fluidized bed. Further, in the case of a fixed bed, it may be either a horizontal fixed bed or a vertical fixed bed, however, in a case where the material gas is a gas mixture consisting of several components, preferred is a vertical fixed bed, whereby concentration distribution of the respective components due to a difference in the specific gravity tends to be prevented.

HFC-134a which is a reaction component in a gaseous phase may be introduced to the reactor as it is at room temperature, however, it is preferably heated (preheated) and then introduced to the reactor, so as to increase the reactivity in the reactor. In a case where it is preheated, HFC-134a is preferably heated to a temperature of from 80 to 450° C. and then supplied to the reactor.

As mentioned above, with a view to suppressing side reaction, HFC-134a is preferably supplied as mixed with the diluent gas, and in the embodiment in which HFC-134a in a gaseous phase is brought into contact with and reacted with calcium oxide in a solid phase, mixing of the diluent gas is preferred also in view of easiness of supply of HFC-134a to the reactor and control of the flow rate.

The material gas containing the diluent gas and HFC-134a is also preferably introduced to the reactor after preheated. HFC-134a and the diluent gas may be respectively preheated to the above temperature and then mixed, and the mixture is supplied to the reactor, or HFC-134a and the diluent gas may be mixed first to form a material gas, and then the material gas is heated to the above temperature and supplied to the reactor.

Further, HFC-134a and the diluent gas may be mixed and the mixture is supplied to the reactor, or they may be separately supplied to the reactor after heated to the above temperature as the case requires.

HFC-134a introduced to the reactor is brought into contact with calcium oxide in a solid phase in the reactor. The temperature at the time of contact of HFC-134a and calcium oxide is preferably from 50 to 500° C., more preferably from 200 to 500° C., most preferably from 300 to 450° C. as the temperature in the reactor, with a view to improving the reactivity. When the temperature in the reactor is at least 300° C., the reaction will be conducted efficiency. When the temperature in the reactor is at most 450° C., side reaction can be suppressed, and the selectivity for 1123 tends to be high. The pressure in the reactor is preferably from 0 to 2 MPa by the gauge pressure. The contact time of HFC-134a and calcium oxide in the reactor is preferably from 0.1 to 500 seconds, more preferably from 0.1 to 100 seconds, further preferably from 0.1 to 20 seconds. Further, in a case where the fixed bed reactor is used, the contact time is particularly preferably from 0.5 to 20 seconds.

(Fixed Bed Reaction Apparatus)

An example of a fixed bed reaction apparatus used for production of HFO-1123 in the present invention is shown in FIG. 1. A fixed bed reaction apparatus 1 shown in FIG. 1 comprises a fixed bed reactor 2 provided with a heating means such as an electric heater. In the fixed bed reactor 2, a heating means is not essential.

In the fixed bed reactor 2, calcium oxide is accommodated to form a solid reactant layer 3. Further, to the fixed bed reactor 2, a preheating mixer 4 provided with a heating means such as an electric heater is connected. The preheating mixer 4 is connected to the fixed bed reactor 2 by means of a material gas supply line 5. To the preheating mixer 4, a HFC-134a supply line 6 to supply HFC-134a which is gaseous at room temperature as a material and a diluent gas supply line 7 to supply a diluent gas are connected. HFC-134a and a diluent gas are supplied to the preheating mixer 4 respectively through the HFC-134a supply line 6 and the diluent gas supply line 7, mixed in the preheating mixer 4 and heated to a predetermined temperature, and the mixture is supplied to the fixed bed reactor 2 through the material gas supply line 5.

Further, the HFC-134a supply line 6 and the diluent gas supply line 7 may be combined before the preheating mixer 4, so that HFC-134a and the diluent gas are mixed and the mixture is supplied to the preheating mixer 4 through a gas mixture supply line. Further, at least one of the HFC-134a supply line 6 and the diluent gas supply line 7 may be provided with a preheater (not shown) provided with e.g. an electric heater, so that at least one of HFC-134a and the diluent gas supplied through the line is preheated and then introduced to the preheating mixer 4.

To the outlet of the fixed bed reactor 2, an outlet line 9 provided with a heating means 8 such as an electric heater is connected, and the outlet line 9 is provided with a hydrogen fluoride trapping tube 10. Hydrogen fluoride is removed from a gas discharged from the outlet of the fluidized bed reactor 2 (hereinafter referred to as an outlet gas) by the hydrogen fluoride trapping tube 10, and the outlet gas is collected into a sampling bag 11, and its components are analyzed by an analyzer such as a gas chromatograph (GC) and determined.

(Fluidized Bed Reaction Apparatus)

Figure 2:
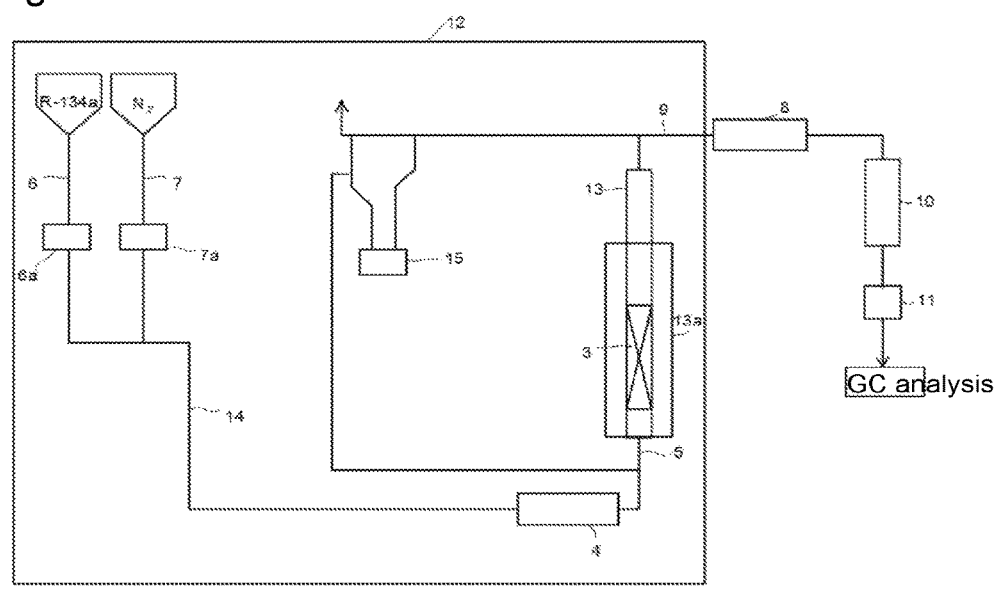
FIG. 2 is a diagram illustrating an example of a fluidized bed reaction apparatus used in the production method of the present invention.

An example of a fluidized bed reaction apparatus used for production of HFO-1123 in the present invention is shown in FIG. 2. A fluidized bed reaction apparatus 12 shown in FIG. 2 comprises a fluidized bed reactor 13 provided with an electric heater 13a as a heating means. In the fluidized bed reactor 13, a heating means is not essential.

In the fluidized bed reactor 13, calcium oxide is accommodated to form a solid reactant layer 3. To the fluidized bed reactor 13, a preheating mixer 4 provided with a heating means such as an electric heater is connected. The preheating means 4 is connected to the fluidized bed reactor 13 by means of a material gas supply line 5. To the preheating mixer 4, a HFC-134a supply line 6 to supply HFC-134a which is gaseous at room temperature as a material and a diluent gas supply line 7 to supply a diluent gas are connected. Further, the HFC-134a supply line 6 and the diluent gas supply line 7 are combined before the preheating mixer 4. HFC-134a and a diluent gas are supplied respectively through the HFC-134a supply line 6 and the diluent gas supply line 7, mixed in a gas mixture supply line 14 and supplied to the preheating mixer 4.

HFC-134a and a diluent gas are mixed and heated to a predetermined temperature in the preheating mixer 4 and supplied to the fluidized bed reactor 13 through a material gas supply line 5.

The HFC-134a supply line 6 and the diluent gas supply line 7 may be respectively connected to the preheating mixer 4, so that HFC-134a and the diluent gas are separately supplied. Further, at least one of the HFC-134a supply line 6 and the diluent gas supply line 7 may be provided with a preheater (not shown) provided with e.g. an electric heater, so that at least one of HFC-134a and the diluent gas supplied through the line is preheated and then introduced to the preheating mixer 4.

To the outlet of the fluidized bed reactor 13, an outlet line 9 provided with a heating means 8 such as an electric heater is connected, and the outlet line 9 mat be provided with a hydrogen fluoride trapping tube 10 as the case requires. A gas discharged from the outlet of the fluidized bed reactor 13 (hereinafter referred to as an outlet gas) is collected into a sampling bag 11, and its components are analyzed by an analyzer such as a gas chromatograph (GC) and determined. On that occasion, the outlet gas may be collected in the sampling bag 11 after hydrogen fluoride is removed by the hydrogen fluoride trapping tube 10 provided as the case requires. Further, in order to confirm the fluidized state of the solid reactant layer 3 (hereinafter sometimes referred to as a fluidized state), a differential pressure gauge 15 is disposed between the material gas supply line 5 and the outlet line 9.

The fluidized state is a state created by extruding a fluid such as a material gas upward (in a direction opposite to the direction of gravitational force) and making it flow, and is a state in which particles of the solid reactant are suspended and floating in the fluid.

The fluidized state of the solid reactant layer 3 may be examined, for example, by measuring a difference in the gas pressure between on the inlet side and on the outlet side of the fluidized bed reactor 13 (hereinafter referred to simply as a differential pressure), plotting the differential pressure relative to the velocity of flow (for example, the after-described linear velocity) of the gas to prepare a graph, and judging the start of fluidization by the presence of an inflection point.

(Outlet Gas Component)

In the production method of the present invention, HFO-1123 can be obtained as a component in the outlet gas. Compounds other than HFO-1123 and an unreacted material component (HFC-134a) contained in the outlet gas may, for example, be hydrogen fluoride, E/Z-1,2-difluoroethylene (E/Z-HFO-1132), 1,1-difluoroethylene (VdF), 1,1,2-trifluoroethane (HFC-143), 1,1,1-trifluoroethane (HFC-143a), methane, ethane, ethylene, propane, propylene, n-butane, isobutane, 1-n-butene, 2-n-butene, isobutene, fluoroethylene (HFO-1141), 3,3-difluoropropene (HFC-1252zf), 3,3,3-trifluoropropene (HFC-1243zf), 2,3,3,3-tetrafluoropropene (HFC-1234yf), E/Z-1,3,3,3-tetrafluoropropene (E/Z-HFC-1234ze), hexafluoropropylene (HFP), HFC-125, HFC-134, 1,1,1-trifluoroethane (HFC-143a), 1,1,1,2,2,3,3-heptafluoropropane (HFC-227ca), 1,1,1,2,3,3,3-heptafluoropropane (HFC-227ea), 1,1,1,3,3,3-hexafluoropropane (HFC-236fa), 1,1,1,2,3,3-hexafluoropropane (HFC-236ea), HFC-32, trifluoromethane (HFC-23), fluoromethane (HFC-41), carbon monoxide, carbon dioxide and water. In the above description, E/Z means a mixture of E-form and Z-form.

The compound obtained as the outlet gas component may be used as it is for various applications, but is preferably used after purification to improve the purity of HFO-1123 as a desired component. The purification method may, for example, be distillation, adsorption or washing with an acidic aqueous solution, a basic aqueous solution or a neutral aqueous solution. The components other than HFO-1123 contained in the outlet gas may be separated and removed to a desired extent by the above means. Among the above purification methods, preferred is distillation under normal pressure, elevated pressure or reduced pressure, and by distillation under such a pressure, high purity HFO-1123 can be obtained. Further, HFC-134a separated from the outlet gas may be recycled as a part of the material gas.

HFO-1123 obtained by the production method of the present invention is useful as a refrigerant which replaces HFC-32 and HFC-125 which are greenhouse gases, and as a material monomer or a synthetic intermediate of a functional material such as a piezoelectric element or a film.

According to the production method of the present invention, it is possible to produce HFO-1123 useful as a new refrigerant and a material monomer or a synthetic intermediate of a functional material, by an efficient method from HFC-134a as a material, with a high degree of conversion of HFC-134a and a high selectivity for HFO-1123 with small loss by formation of impurities. Further, HFO-1123 can be produced with a high yield stably over a long period of time without causing clogging of the reactor or a decrease in the yield of a product, with a light load to the subsequent process.

EXAMPLES

Now, the present invention will be described in detail with reference to Examples. However, it should be understood that the present invention is by no means restricted to such specific Examples.

A. Reaction Using Fixed Bed Reaction Apparatus (Analysis Conditions)

To analyze the composition of the outlet gas, gas chromatography (GC) was employed. As a column, DB-1

(length: 60 m×inner diameter: 250 μm×thickness: 1 μm, manufactured by Agilent Technologies) was used.
(Fixed Bed Reaction Apparatus)

As a fixed bed reaction apparatus, a fixed bed reaction apparatus 1 shown in FIG. 1 was used. As a fixed bed reactor 2, a vertical reactor having an inner diameter of 21.4 mm and a height of 600 mm made of stainless steel (SUS316) was used, a SUS316 insertion tube having a diameter of 3.1 mm was introduced to the center of the reactor, a type K thermocouple was inserted to the insertion tube, and the temperature in the reactor was measured. Further, a grating and glass wool were disposed at a height of 100 mm from the lower portion of the reactor, and a reactant was packed thereon with a height of 150 mm. Further, the interior of the fixed bed reactor was heated by an electric furnace. As a reactant, as described hereinafter, calcium oxide was used in Examples 1 to 5, and calcium hydroxide was used in Comparative Examples 1 to 5.

Further, a preheating mixer to which a material gas supply line was connected was connected to the lower portion of the fixed bed reactor, and the material gas supply line and the preheating mixer were respectively heated to 100° C. by a ribbon heater. The flow rates of HFC-134a and nitrogen as a diluent gas were adjusted respectively by mass flow controllers and they were supplied to the preheating mixer through a HFC-134a supply line and a diluent gas supply line. The outlet gas containing a reaction product was continuously withdrawn from the upper portion of the fixed bed reactor, made to flow through a hydrogen fluoride trapping tube packed with 28 g of 1/16 inch sodium fluoride pellets, collected in a sampling bag 11 made of polyvinylidene fluoride (PVdF) (hereinafter referred to as a PVdF bag), and analyzed by means of gas chromatography (GC). The temperature and the pressure in the fixed bed reactor as described hereinafter are measured values.

Reactant Packing/Drying Example 1

The fixed bed reactor 2 of the fixed bed reaction apparatus 1 was packed with 45 g (798 mmol) of powdery calcium oxide (average particle size: 10 μm, bulk density: 0.74 g/cm$^3$, specific surface area: 2.2 m$^2$/g) (manufactured by KANTO CHEMICAL CO., LTD., tradename: calcium oxide 3N (high purity reagent grade)) to a height of 150 mm. The interior of the fixed bed reactor was heated at a temperature of 310° C. for 2 hours while a nitrogen gas was made to flow through the fixed bed reactor at a flow rate per unit time (hereinafter referred to as simply as a flow rate) of 27.1 mmol/min via the diluent gas supply line, to dry calcium oxide.

Reactant Packing/Drying Example 2

The fixed bed reactor 2 of the fixed bed reaction apparatus 1 was packed with 26 g (351 mmol) of powdery calcium hydroxide (average particle size: 5 μm, bulk density: 0.56 g/cm$^3$, specific surface area: 7.8 m$^2$/g) (manufactured by KANTO CHEMICAL CO., LTD., tradename: calcium hydroxide (special grade)) to a height of 150 mm. The interior of the fixed bed reactor was heated at a temperature of 310° C. for 2 hours while a nitrogen gas was made to flow through the fixed bed reactor at a flow rate of 13.5 mmol/min via the diluent gas supply line, to dry calcium hydroxide.

Example 1

The temperature in the fixed bed reactor was kept at 310° C. while a nitrogen gas was made to flow at a flow rate of 6.77 mmol/min through the fixed bed reactor 2 having calcium oxide packed and dried in Reactant Packing/Drying Example 1. Further, without terminating the flow of the nitrogen gas, HFC-134a was started to be made to flow at a flow rate of 0.34 mmol/min by the HFC-134a supply line, and immediately after the start of the flow, the flow rate of the nitrogen gas was changed to 6.43 mmol/min. HFC-134a was made to flow and reacted with calcium oxide for 15 minutes after the start of the flow, and then supply of HFC-134a was terminated, the flow rate of the nitrogen gas was changed to 6.77 mmol/min, and the reaction was completed. The outlet gas from 5 minutes after the start of the flow of HFC-134a to the completion of the reaction was continuously collected in a sampling bag made of polyvinylidene fluoride (PVdF) (hereinafter referred to as a PVdF bag). The composition of the collected outlet gas was analyzed by gas chromatography. The analysis results are shown in Table 1 together with the reaction conditions (the nitrogen flow rate before the reaction, the reaction temperature, the HFC-134a flow rate at the time of the reaction, the nitrogen flow rate at the time of the reaction, the reaction molar ratio (HFC-134a:nitrogen), the linear velocity at the time of the reaction, the contact time at the time of the reaction and the time over which HFC-134a was made to flow (hereinafter referred to as the reaction time)).

Examples 2 to 5

Examples 2 to 5 were sequentially carried out without exchanging calcium oxide in the fixed bed reactor, after completion of the reaction in Example 1 until completion of Example 5. In Examples 2 to 5, HFC-134a was reacted with calcium oxide in the same manner as in Example 1 except that the reaction conditions were changed as identified in Table 1. The composition of the outlet gas collected was analyzed by gas chromatography. The analysis results are shown in Table 1.

Comparative Example 1

The temperature in the fixed bed reactor was kept at 310° C. while a nitrogen gas was made to flow at a flow rate of 6.77 mmol/min through the fixed bed reactor 2 having calcium hydroxide packed and dried in Reactant Packing/Drying Example 2. Further, without terminating the flow of the nitrogen gas, HFC-134a was started to be made to flow at a flow rate of 0.34 mmol/min by the HFC-134a supply line, and immediately after the start of the flow, the flow rate of the nitrogen gas was changed to 6.43 mmol/min. HFC-134a was made to flow and reacted with calcium hydroxide for 15 minutes after the start of the flow, and then supply of HFC-134a was terminated, the flow rate of the nitrogen gas was changed to 6.77 mmol/min, and the reaction was completed. The outlet gas thus obtained from 5 minutes after the start of the flow of HFC-134a to the completion of the reaction was continuously collected in a PVdF bag. The composition of the collected outlet gas was analyzed by gas chromatography. The analysis results are shown in Table 2 together with the reaction conditions.

Comparative Examples 2 to 5

Comparative Examples 2 to 5 were sequentially carried out without exchanging calcium hydroxide in the fixed bed reactor after completion of the reaction in Comparative Example 1 until completion of Comparative Example 5. In Comparative Examples 2 to 5, HFC-134a was brought into contact with and reacted with calcium hydroxide in the same manner as in Comparative Example 1 except that the reaction conditions were changed as identified in Table 2. The composition of the collected outlet gas was analyzed by gas chromatography. The analysis results are shown in Table 2.

Then, in Examples 1 to 5 and Comparative Examples 1 to 5, based on the area ratio (GC Area %) of the outlet gas obtained by gas chromatography analysis, the degree of conversion (reactivity) of HFC-134a, the selectivity for HFO-1123 and the selectivity for other gases were obtained as follows. In the following formulae, (HFC-134a) and (HFO-1123) respectively represent the area ratios (%) of (HFC-134a) and (HFO-1123) in the outlet gas.

The results are shown in the lower rows in Table 1 with respect to Examples 1 to 5 and in the lower rows in Table 2 with respect to Comparative Examples 1 to 5.

[Degree of Conversion (%) of HFC-134a]

It represents the proportion of components other than HFC-134a among components derived from HFC-134a in the outlet gas. It is calculated from {100−(HFC-134a)}/100× 100(%) in the outlet gas.

[Selectivity (%) for HFO-1123]

It represents the proportion of HFC-134a converted to HFO-1123 based on the entire HFC-134a reacted, represented by %. It is calculated from (HFO-1123)/{100−(HFC-134a)}×100(%) in the outlet gas.

[Selectivity (%) for Other Gases]

It represents the proportion of HFC-134a converted to compounds other than HFO-1123 based on the entire HFC-134a reacted, represented by %. It is calculated from {100−(HFC-134a)−(HFO-1123)}/{100−(HFC-134a)}×100(%) in the outlet gas.

TABLE 1

| | | Example 1 | Example 2 | Example 3 | Example 4 | Example 5 |
|---|---|---|---|---|---|---|
| Reactant | | Calcium oxide | | | | |
| Reactant packing amount (g) | | 45 | | | | |
| Reactant packing amount (mmol) | | 798 | | | | |
| Nitrogen flow rate before reaction (mmol/min) | | 6.77 | 6.24 | 5.78 | 5.78 | 5.79 |
| Reaction temperature (° C.) | | 310 | 360 | 410 | 410 | 410 |
| HFC-134a flow rate at the time of reaction (mmol/min) | | 0.34 | 0.31 | 1.16 | 2.89 | 5.79 |
| Nitrogen flow rate at the time of reaction (mmol/min) | | 6.43 | 5.92 | 4.62 | 2.89 | 0.00 |
| Composition ratio at the time of reaction HFC-134a:N2 (molar ratio) | | 5:95 | 5:95 | 20:80 | 50:50 | 100:0 |
| Linear velocity at the time of reaction (cm/s) | | 1.5 | 1.5 | 1.5 | 1.5 | 1.5 |
| Contact time at the time of reaction (s) | | 10.0 | 10.0 | 10.0 | 10.0 | 10.0 |
| Reaction time (min) | | 15 | 15 | 15 | 15 | 15 |
| Structure | Name | Outlet gas composition (other than nitrogen) (area %) | | | | |
| $CF_2=CHF$ | HFO-1123 | 14.6 | 29.4 | 36.7 | 19.9 | 11.8 |
| $CF_3CH_2F$ | HFC-134a | 85.1 | 70.0 | 62.4 | 79.8 | 88.0 |
| Others | | 0.3 | 0.6 | 0.9 | 0.2 | 0.1 |
| Degree of conversion of HFC-134a (%) | | 14.9 | 30.0 | 37.6 | 20.2 | 12.0 |
| Selectivity for HFO-1123 (%) | | 98.0 | 98.0 | 97.7 | 98.8 | 98.8 |
| Selectivity for other gases (%) | | 2.0 | 2.0 | 2.3 | 1.2 | 1.2 |

TABLE 2

| | | Comparative Example 1 | Comparative Example 2 | Comparative Example 3 | Comparative Example 4 | Comparative Example 5 |
|---|---|---|---|---|---|---|
| Reactant | | Calcium hydroxide | | | | |
| Reactant packing amount (g) | | 26 | | | | |
| Reactant packing amount (mmol) | | 351 | | | | |
| Nitrogen flow rate before reaction (mmol/min) | | 6.77 | 6.24 | 5.78 | 5.78 | 5.78 |
| Reaction temperature (° C.) | | 310 | 360 | 410 | 410 | 410 |
| HFC-134a flow rate at the time of reaction (mmol/min) | | 0.34 | 0.31 | 1.16 | 2.89 | 5.78 |
| Nitrogen flow rate at the time of reaction (mmol/min) | | 6.43 | 5.92 | 4.62 | 2.89 | 0.00 |
| Composition ratio at the time of reaction HFC-134a:N2 (molar ratio) | | 5:95 | 5:95 | 20:80 | 50:50 | 100:0 |
| Linear velocity at the time of reaction (cm/s) | | 1.5 | 1.5 | 1.5 | 1.5 | 1.5 |
| Contact time at the time of reaction (s) | | 10.0 | 10.0 | 10.0 | 10.0 | 10.0 |
| Reaction time (min) | | 15 | 15 | 15 | 12 | 15 |
| Structure | Name | Outlet gas composition (other than nitrogen) (area %) | | | | |
| $CF_2=CHF$ | HFO-1123 | 19.5 | 43.0 | 42.6 | 26.1 | 14.0 |
| $CF_3CH_2F$ | HFC-134a | 80.1 | 56.0 | 54.8 | 73.1 | 85.6 |
| Others | | 0.4 | 1.0 | 2.6 | 0.9 | 0.3 |
| Degree of conversion of HFC-134a (%) | | 19.9 | 44.0 | 45.2 | 26.9 | 14.4 |
| Selectivity for HFO-1123 (%) | | 97.8 | 97.7 | 94.3 | 96.8 | 97.7 |
| Selectivity for other gases (%) | | 2.2 | 2.3 | 5.7 | 3.2 | 2.3 |

B. Reaction Using Fluidized Bed Reaction Apparatus
(Analysis Conditions)

The composition of the outlet gas was analyzed in the same manner as in Example 1.

(Fluidized Bed Reaction Apparatus)

As a fluidized bed reaction apparatus, a fluidized bed reaction apparatus 12 shown in FIG. 2 was used. The fluidized bed reaction apparatus 12 comprises a fluidized bed reactor 13 capable of fluidizing a powder, and is provided with a differential pressure measuring device to measure a differential pressure between on the inlet side and on the outlet side of the fluidized bed reactor. As the fluidized bed reactor 13, a reactor for a vertical fluidized bed having an inner diameter of 106.3 mm and a height of 550 mm made of stainless steel (SUS316) was used, a SUS316 insertion tube having a diameter of 6 mm was introduced in the vertical direction, a type K thermocouple was inserted to the insertion tube, and the temperature in the reactor was measured. Further, a grating was disposed at the lowest portion of the fluidized bed reactor 13, and a solid reactant was packed thereon to form a solid reactant layer 3. The interior of the fluidized bed reactor 13 was heated by an electric heater 13a.

A preheating mixer 4 was connected to the lower portion of the fluidized bed reactor 13 via a material gas supply line 5. The material gas supply line 5 and the preheating mixer 4 were respectively heated to 200 to 450° C. by a ribbon heater. The apparatus was so constituted that HFC-134a and nitrogen as a diluent gas were mixed while their flow rates were adjusted respectively by mass flow controllers 6a and 7a provided to a HFC-134a supply line 6 and a diluent gas supply line 7, and the gas mixture was supplied to the preheating mixer 4 through a gas mixture supply line 14. The outlet gas containing a reaction product was continuously withdrawn from the upper portion of the fluidized bed reactor 13, collected in a sampling bag 11 made of polyvinylidene fluoride (PVdF) (hereinafter referred to as a PVdF bag), and subjected to composition analysis by means of gas chromatography (GC).

Further, the differential pressure measuring device was constituted as follows. That is, a digital differential pressure gauge 15 was disposed between an outlet side piping connected to the lower portion of the fluidized bed reactor 13 and an outlet side piping connected to the upper portion.

The fluidized state of the solid reactant layer 3 was confirmed by a method in which the differential pressure of the fluidized bed reactor 13 was measured, the differential pressure relative to the linear velocity of the gas was plotted to prepare a graph, and the start of fluidization was judged by the presence of an inflection point.

Reactant Packing Example 3

The fluidized bed reactor 13 of the fluidized bed reaction apparatus 12 was packed with 2,099 g (37.42 mol) of powdery calcium oxide (average particle size: 100 μm, bulk density: 1.2 g/cm$^3$, specific surface area: 2.9 m$^2$/g (hereinafter referred to as calcium oxide)) as a solid reactant to a height of 200 mm.

Reactant Packing Example 4

The fluidized bed reactor 13 of the fluidized bed reaction apparatus 12 was packed with 3,143 g (56.05 mol) of powdery calcium oxide (average particle size: 100 μm, bulk density: 1.2 g/cm$^3$, specific surface area: 2.9 m$^2$/g (hereinafter referred to as calcium oxide)) as a solid reactant to a height of 300 mm.

(Linear Velocity)

The linear velocity of each of the nitrogen gas, HFC-134a and the gas mixture of nitrogen and HFC-134a was obtained by dividing the flow rate (volume flow rate) per unit time of each gas by the cross section area of the fluidized bed reactor 13.

Blank Differential Pressure Measurement Example 1

The differential pressure when a nitrogen gas was made to flow through the empty fluidized bed reactor 13 before packed with the reactant of the fluidized bed reaction apparatus 12 at a flow rate of 3.92 mol/min (linear velocity of 18 cm/s) at room temperature (25° C.) under normal pressure was measured. On that occasion, the differential pressure between on the inlet side and on the outlet side of the fluidized bed reactor measured by the differential pressure gauge was 10,900 Pa. Then, the nitrogen gas flow rate was gradually decreased, and the differential pressure between on the inlet side and on the outlet side of the fluidized bed reactor was measured by the differential pressure gauge at each flow rate.

Blank Differential Pressure Measurement Example 2

The differential pressure when HFC-134a was made to flow through the empty fluidized bed reactor 13 before packed with the reactant of the fluidized bed reaction apparatus 12 at a flow rate of 2.61 mol/min (linear velocity of 12 cm/s) at room temperature (25° C.) under normal pressure was measured. On that occasion, the differential pressure between on the inlet side and on the outlet side of the fluidized bed reactor measured by the differential pressure gauge was 11,500 Pa. Then, the HFC-134a flow rate was gradually decreased, and the differential pressure between on the inlet side and on the outlet side of the fluidized bed reactor was measured by the differential pressure gauge at each flow rate.

Blank Differential Pressure Measurement Example 3

The differential pressure when a nitrogen gas was made to flow through the empty fluidized bed reactor 13 before packed with the reactant of the fluidized bed reaction apparatus 12 at a flow rate of 2.47 mol/min (linear velocity of 18 cm/s) at 200° C. under normal pressure was measured. On that occasion, the differential pressure between on the inlet side and on the outlet side of the fluidized bed reactor measured by the differential pressure gauge was 11,700 Pa. Then, the nitrogen gas flow rate was gradually decreased, and the differential pressure between on the inlet side and on the outlet side of the fluidized bed reactor was measured by the differential pressure gauge at each flow rate.

Blank Differential Pressure Measurement Example 4

The differential pressure when a nitrogen gas was made to flow through the empty fluidized bed reactor 13 before packed with the reactant of the fluidized bed reaction apparatus 12 at a flow rate of 1.25 mol/min (linear velocity of 11 cm/s) at 300° C. under normal pressure was measured. On that occasion, the differential pressure between on the inlet side and on the outlet side of the fluidized bed reactor measured by the differential pressure gauge was 6,500 Pa. Then, the nitrogen gas flow rate was gradually decreased, and the differential pressure between on the inlet side and on the outlet side of the fluidized bed reactor was measured by the differential pressure gauge at each flow rate.

Reactant Packing Example 3

The fluidized bed reactor 13 of the fluidized bed reaction apparatus 12 was packed with 2,099 g (37.42 mol) of particulate calcium oxide (average particle size: 100 μm, bulk density: 1.2 g/cm$^3$, specific surface area: 2.9 m$^2$/g (hereinafter referred to as calcium oxide)) as a solid reactant to a height of 200 mm.

Reactant Packing Example 4

The fluidized bed reactor 13 of the fluidized bed reaction apparatus 12 was packed with 3,143 g (56.05 mol) of particulate calcium oxide (average particle size: 100 μm, bulk density: 1.2 g/cm$^3$, specific surface area: 2.9 m$^2$/g (hereinafter referred to as calcium oxide)) as a solid reactant to a height of 300 mm.

In the following Fluidization Examples 1 to 5, the fluidization starting velocity was determined in accordance with the calculated differential pressure obtained by subtracting the blank differential pressure before packing with the reactant from the differential pressure after packing with the reactant (hereinafter referred to as differential pressure after packing) under the same conditions (the temperature, the pressure, the type of the gas, the flow rate). In a graph obtained by plotting the calculated differential pressure relative to the linear velocity of the gas, the inflection point at which the gradient of the graph changes is taken as the starting point of fluidization of the solid reactant layer, and the linear velocity at the inflection point is taken as the complete fluidization starting velocity.

Fluidization Example 1

Through the fluidized bed reaction apparatus packed with the solid reactant (calcium oxide having an average particle size of 100 μm) to a height of 200 mm shown in Reactant Packing Example 3, a nitrogen gas was made to flow at a flow rate of 3.05 mol/min (linear velocity of 14 cm/s) at room temperature (25° C.) under normal pressure. On that occasion, the differential pressure between on the inlet side and on the outlet side of the fluidized bed reactor measured by the differential pressure gauge was 10,900 Pa.

Figure 3:
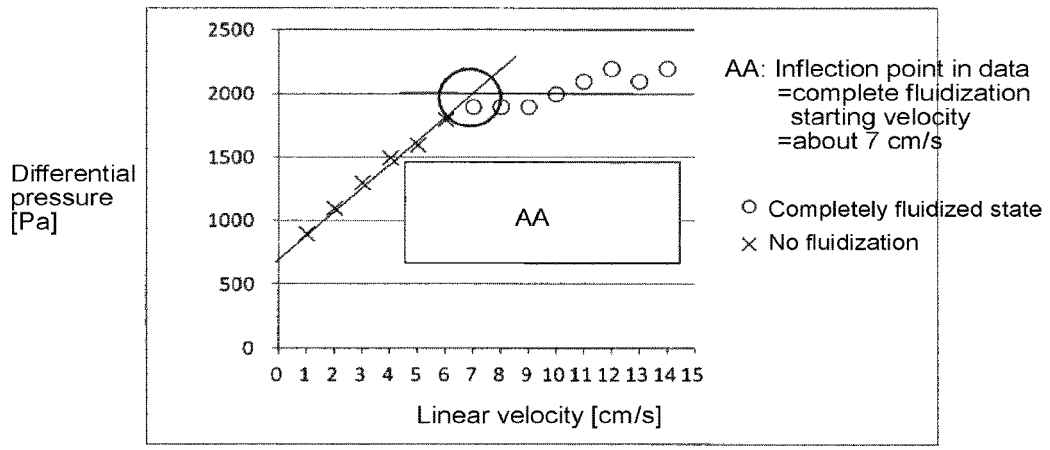
FIG. 3 is a graph obtained by plotting a differential pressure relative to a linear velocity of a nitrogen gas in Fluidization Example 1.

Then, the nitrogen gas flow rate was gradually decreased, and the differential pressure between on the inlet side and on the outlet side of the fluidized bed reactor was measured by the differential pressure gauge at each flow rate. The flow rate of the nitrogen gas, the linear velocity, the measured differential pressure after packing, and the calculated differential pressure obtained by calculating the difference with the Blank Differential Pressure Measurement Example 1 are shown in Table 3. Further, a graph obtained by plotting the calculated differential pressure relative to the linear velocity of the nitrogen gas is shown in FIG. 3. It can be judged from Table 3 and FIG. 3 that in Fluidization Example 1, the complete fluidization starting velocity of the solid reactant layer is 7 cm/s.

TABLE 3

| Fluidization Example 1 | | | | | | | |
|---|---|---|---|---|---|---|---|
| Type of reactant ° C. | Calcium oxide | | | | | | |
| Reactant packing height mm | 200 | | | | | | |
| Temperature ° C. | 25 | | | | | | |
| Gas composition ratio — HFC-134a mol % | 0 | | | | | | |
| Gas composition ratio — Nitrogen mol % | 100 | | | | | | |
| Flow rate — HFC-134a mol/min | 0.00 | 0.00 | 0.00 | 0.00 | 0.00 | 0.00 | 0.00 |
| Flow rate — Nitrogen mol/min | 3.05 | 2.83 | 2.61 | 2.39 | 2.18 | 1.96 | 1.74 |
| Linear velocity cm/s | 14 | 13 | 12 | 11 | 10 | 9 | 8 |
| Differential pressure after packing Pa | 10900 | 10000 | 9300 | 8500 | 7700 | 6900 | 6100 |
| Blank differential pressure Pa | 8700 | 7900 | 7100 | 6400 | 5700 | 5000 | 4200 |
| Calculated differential pressure Pa | 2200 | 2100 | 2200 | 2100 | 2000 | 1900 | 1900 |
| Type of reactant ° C. | Calcium oxide | | | | | | |
| Reactant packing height mm | 200 | | | | | | |
| Temperature ° C. | 25 | | | | | | |
| Gas composition ratio — HFC-134a mol % | 0 | | | | | | |
| Gas composition ratio — Nitrogen mol % | 100 | | | | | | |
| Flow rate — HFC-134a mol/min | 0.00 | 0.00 | 0.00 | 0.00 | 0.00 | 0.00 | 0.00 |
| Flow rate — Nitrogen mol/min | 1.52 | 1.31 | 1.09 | 0.87 | 0.65 | 0.44 | 0.22 |
| Linear velocity cm/s | 7 | 6 | 5 | 4 | 3 | 2 | 1 |
| Differential pressure after packing Pa | 5400 | 4700 | 3900 | 3300 | 2500 | 1900 | 1200 |
| Blank differential pressure Pa | 3500 | 2900 | 2300 | 1800 | 1200 | 800 | 300 |
| Calculated differential pressure Pa | 1900 | 1800 | 1600 | 1500 | 1300 | 1100 | 900 |

*Blank Differential Pressure Measurement Example 1 was employed.

Fluidization Example 2

Through the fluidized bed reaction apparatus packed with the solid reactant (calcium oxide having an average particle size of 100 μm) to a height of 300 mm shown in Reactant Packing Example 4, a nitrogen gas was made to flow at a flow rate of 2.83 mol/min (linear velocity of 13 cm/s) at room temperature (25° C.) under normal pressure. On that occasion, the differential pressure between on the inlet side and on the outlet side of the fluidized bed reactor measured by the differential pressure gauge was 10,200 Pa.

Figure 4:
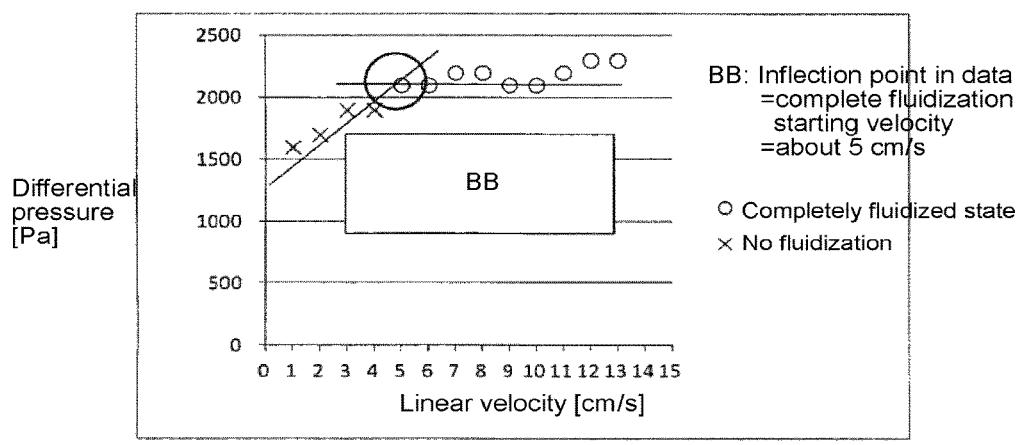
FIG. 4 is a graph obtained by plotting a differential pressure relative to a linear velocity of a nitrogen gas in Fluidization Example 2.

Then, the nitrogen gas flow rate was gradually decreased, and the differential pressure between on the inlet side and on the outlet side of the fluidized bed reactor was measured by the differential pressure gauge at each flow rate. The flow rate of the nitrogen gas, the linear velocity, the measured differential pressure after packing, and the calculated differential pressure obtained by calculating the difference with the Blank Differential Pressure Measurement Example 1 are shown in Table 4. Further, a graph obtained by plotting the calculated differential pressure relative to the linear velocity of the nitrogen gas is shown in FIG. 4. It can be judged from Table 4 and FIG. 4 that in Fluidization Example 2, the complete fluidization starting velocity of the solid reactant layer is 5 cm/s.

size of 100 μm) to a height of 200 mm shown in Reactant Packing Example 3, HFC-134a was made to flow at a flow rate of 2.61 mol/min (linear velocity of 12 cm/s) at room temperature (25° C.) under normal pressure. On that occasion, the differential pressure between on the inlet side and on the outlet side of the fluidized bed reactor measured by the differential pressure gauge was 13,400 Pa.

Figure 5:
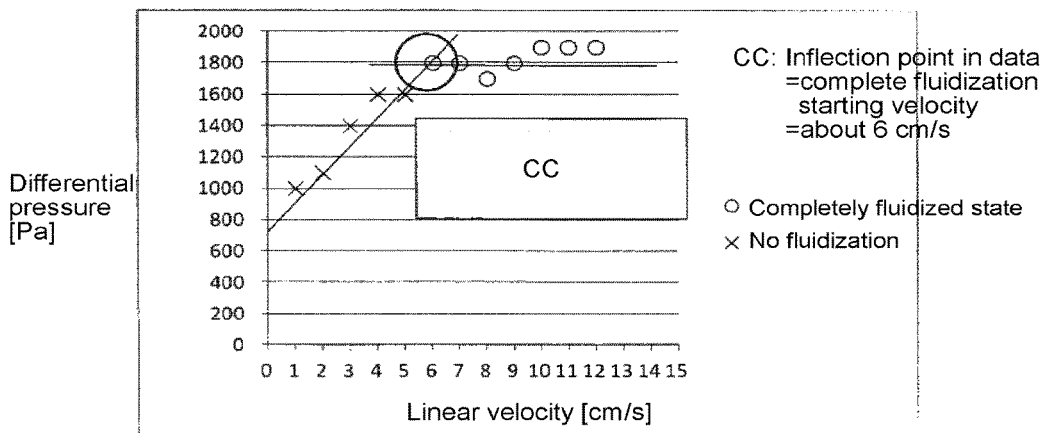
FIG. 5 is a graph obtained by plotting a differential pressure relative to a linear velocity of HFC-134a in Fluidization Example 3.

Then, the HFC-134a flow rate was gradually decreased, and the differential pressure between on the inlet side and on the outlet side of the fluidized bed reactor was measured by the differential pressure gauge at each flow rate. The flow rate of HFC-134a, the linear velocity, the measured differential pressure after packing, and the calculated differential pressure obtained by calculating the difference with the Blank Differential Pressure Measurement Example 2 are shown in Table 5. Further, a graph obtained by plotting the calculated differential pressure relative to the linear velocity of HFC-134a is shown in FIG. 5. It can be judged from Table 5 and FIG. 5 that in Fluidization Example 3, the complete fluidization starting velocity of the solid reactant layer is 6 cm/s.

TABLE 4

Fluidization Example 2

| Type of reactant ° C. | | | | | | Calcium oxide | | | | | | | |
|---|---|---|---|---|---|---|---|---|---|---|---|---|---|
| Reactant packing height mm | | | | | | 300 | | | | | | | |
| Temperature ° C. | | | | | | 25 | | | | | | | |
| Gas composition ratio | HFC-134a mol % | | | | | 0 | | | | | | | |
| | Nitrogen mol % | | | | | 100 | | | | | | | |
| Flow rate | HFC-134a mol/min | 0.00 | 0.00 | 0.00 | 0.00 | 0.00 | 0.00 | 0.00 | 0.00 | 0.00 | 0.00 | 0.00 | 0.00 | 0.00 |
| | Nitrogen mol/min | 2.83 | 2.61 | 2.39 | 2.18 | 1.96 | 1.74 | 1.52 | 1.31 | 1.09 | 0.87 | 0.65 | 0.44 | 0.22 |
| Linear velocity cm/s | | 13 | 12 | 11 | 10 | 9 | 8 | 7 | 6 | 5 | 4 | 3 | 2 | 1 |
| Differential pressure after packing Pa | | 10200 | 9400 | 8600 | 7800 | 7100 | 6400 | 5700 | 5000 | 4400 | 3700 | 3100 | 2500 | 1900 |
| Blank differential pressure Pa | | 7900 | 7100 | 6400 | 5700 | 5000 | 4200 | 3500 | 2900 | 2300 | 1800 | 1200 | 800 | 300 |
| Calculated differential pressure Pa | | 2300 | 2300 | 2200 | 2100 | 2100 | 2200 | 2200 | 2100 | 2100 | 1900 | 1900 | 1700 | 1600 |

*Blank Differential Pressure Measurement Example 1 was employed.

Fluidization Example 3

Through the fluidized bed reaction apparatus packed with the solid reactant (calcium oxide having an average particle

TABLE 5

Fluidization Example 3

| Type of reactant ° C. | | | | | | Calcium oxide | | | | | | | |
|---|---|---|---|---|---|---|---|---|---|---|---|---|---|
| Reactant packing height mm | | | | | | 200 | | | | | | | |
| Temperature ° C. | | | | | | 25 | | | | | | | |
| Gas composition ratio | HFC-134a mol % | | | | | 100 | | | | | | | |
| | Nitrogen mol % | | | | | 0 | | | | | | | |
| Flow rate | HFC-134a mol/min | 2.61 | 2.39 | 2.18 | 1.96 | 1.74 | 1.52 | 1.31 | 1.09 | 0.87 | 0.65 | 0.44 | 0.22 |
| | Nitrogen mol/min | 0.00 | 0.00 | 0.00 | 0.00 | 0.00 | 0.00 | 0.00 | 0.00 | 0.00 | 0.00 | 0.00 | 0.00 |
| Linear velocity cm/s | | 12 | 11 | 10 | 9 | 8 | 7 | 6 | 5 | 4 | 3 | 2 | 1 |
| Differential pressure after packing Pa | | 13400 | 12200 | 10900 | 9600 | 8400 | 7200 | 6200 | 5000 | 3900 | 2900 | 2000 | 1300 |
| Blank differential pressure Pa | | 11500 | 10300 | 9000 | 7800 | 6700 | 5400 | 4400 | 3400 | 2300 | 1500 | 900 | 300 |

TABLE 5-continued

| | | | | | | | | | | | | |
|---|---|---|---|---|---|---|---|---|---|---|---|---|
| | Fluidization Example 3 | | | | | | | | | | | |
| Calculated differential pressure Pa | 1900 | 1900 | 1900 | 1800 | 1700 | 1800 | 1800 | 1600 | 1600 | 1400 | 1100 | 1000 |

*Blank Differential Pressure Measurement Example 2 was employed.

Fluidization Example 4

Through the fluidized bed reaction apparatus packed with the solid reactant (calcium oxide having an average particle size of 100 μm) to a height of 200 mm shown in Reactant Packing Example 3, a nitrogen gas was made to flow at a flow rate of 2.19 mol/min (linear velocity of 16 cm/s) at 200° C. under normal pressure. On that occasion, the differential pressure between on the inlet side and on the outlet side of the fluidized bed reactor measured by the differential pressure gauge was 11,200 Pa.

Figure 6:
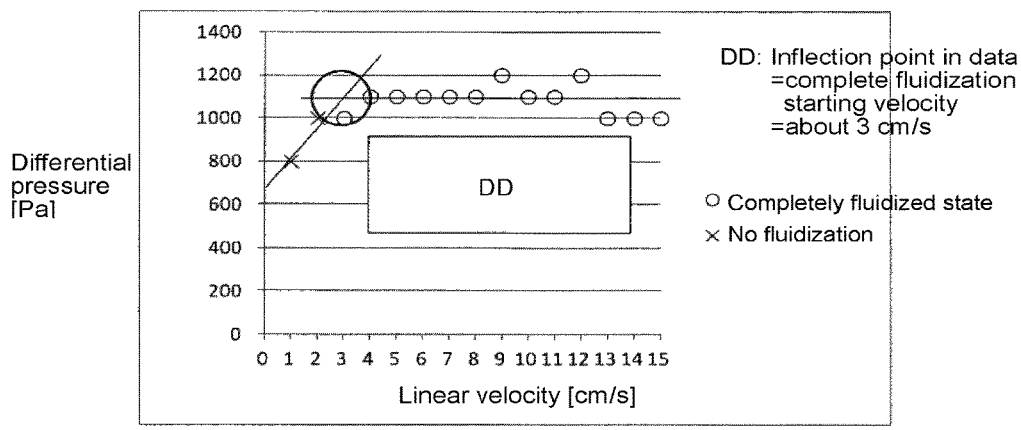
FIG. 6 is a graph obtained by plotting a differential pressure relative to a linear velocity of a nitrogen gas in Fluidization Example 4.

Then, the nitrogen gas flow rate was gradually decreased, and the differential pressure between on the inlet side and on the outlet side of the fluidized bed reactor was measured by the differential pressure gauge at each flow rate. The flow rate of the nitrogen gas, the linear velocity, the measured differential pressure after packing, and the calculated differential pressure obtained by calculating the difference with the Blank Differential Pressure Measurement Example 3 are shown in Table 6. Further, a graph obtained by plotting the calculated differential pressure relative to the linear velocity of the nitrogen gas is shown in FIG. 6. It can be judged from Table 6 and FIG. 6 that in Fluidization Example 4, the complete fluidization starting velocity of the solid reactant layer is 3 cm/s.

Fluidization Example 5

Through the fluidized bed reaction apparatus packed with the solid reactant (calcium oxide having an average particle size of 100 μm) to a height of 200 mm shown in Reactant Packing Example 3, a nitrogen gas was made to flow at a flow rate of 1.25 mol/min (linear velocity of 11 cm/s) at 300° C. under normal pressure. On that occasion, the differential pressure between on the inlet side and on the outlet side of the fluidized bed reactor measured by the differential pressure gauge was 7,700 Pa.

Figure 7:
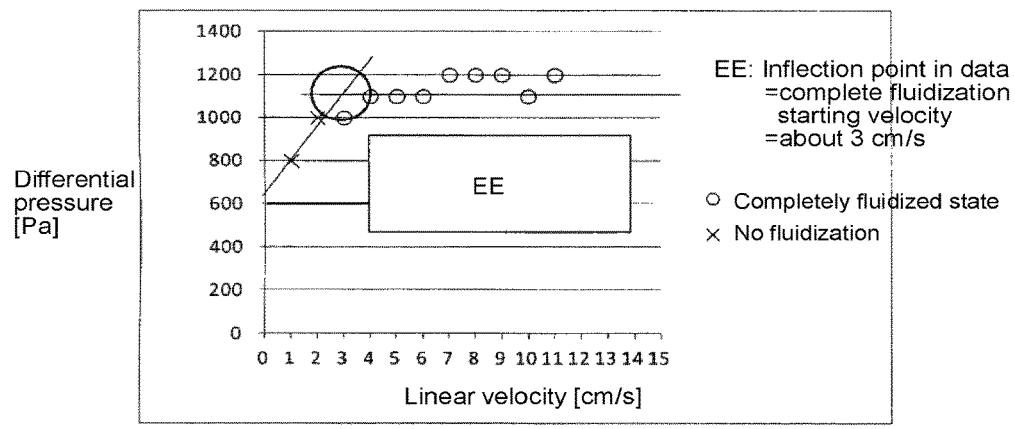
FIG. 7 is a graph obtained by plotting a differential pressure relative to a linear velocity of a nitrogen gas in Fluidization Example 5.

Then, the nitrogen gas flow rate was gradually decreased, and the differential pressure between on the inlet side and on the outlet side of the fluidized bed reactor was measured by the differential pressure gauge at each flow rate. The flow rate of the nitrogen gas, the linear velocity, the measured differential pressure after packing, and the calculated differential pressure obtained by calculating the difference with the Blank Differential Pressure Measurement Example 4 are shown in Table 7. Further, a graph obtained by plotting the calculated differential pressure relative to the linear velocity of the nitrogen gas is shown in FIG. 7. It can be judged from Table 7 and FIG. 7 that in Fluidization Example 5, the complete fluidization starting velocity of the solid reactant layer is 3 cm/s.

TABLE 6

| | Fluidization Example 4 | | | | | | | |
|---|---|---|---|---|---|---|---|---|
| Type of reactant ° C. | Calcium oxide | | | | | | | |
| Reactant packing height mm | 200 | | | | | | | |
| Temperature ° C. | 200 | | | | | | | |
| Gas composition ratio — HFC-134a mol % | 0 | | | | | | | |
| Gas composition ratio — Nitrogen mol % | 100 | | | | | | | |
| Flow rate — HFC-134a mol/min | 0.00 | 0.00 | 0.00 | 0.00 | 0.00 | 0.00 | 0.00 | 0.00 |
| Flow rate — Nitrogen mol/min | 2.19 | 2.06 | 1.92 | 1.78 | 1.65 | 1.51 | 1.37 | 1.23 |
| Linear velocity cm/s | 16 | 15 | 14 | 13 | 12 | 11 | 10 | 9 |
| Differential pressure after packing Pa | 11200 | 10500 | 9800 | 9100 | 8500 | 7700 | 7000 | 6300 |
| Blank differential pressure Pa | 10100 | 9500 | 8800 | 8100 | 7300 | 6600 | 5900 | 5100 |
| Calculated differential pressure Pa | 1100 | 1000 | 1000 | 1000 | 1200 | 1100 | 1100 | 1200 |
| Type of reactant ° C. | Calcium oxide | | | | | | | |
| Reactant packing height mm | 200 | | | | | | | |
| Temperature ° C. | 200 | | | | | | | |
| Gas composition ratio — HFC-134a mol % | 0 | | | | | | | |
| Gas composition ratio — Nitrogen mol % | 100 | | | | | | | |
| Flow rate — HFC-134a mol/min | 0.00 | 0.00 | 0.00 | 0.00 | 0.00 | 0.00 | 0.00 | 0.00 |
| Flow rate — Nitrogen mol/min | 1.10 | 0.96 | 0.82 | 0.69 | 0.55 | 0.41 | 0.27 | 0.14 |
| Linear velocity cm/s | 8 | 7 | 6 | 5 | 4 | 3 | 2 | 1 |
| Differential pressure after packing Pa | 5600 | 4900 | 4300 | 3700 | 3100 | 2400 | 1900 | 1200 |
| Blank differential pressure Pa | 4500 | 3800 | 3200 | 2600 | 2000 | 1400 | 900 | 400 |
| Calculated differential pressure Pa | 1100 | 1100 | 1100 | 1100 | 1100 | 1000 | 1000 | 800 |

*Blank Differential Pressure Measurement Example 3 was employed.

TABLE 7

Fluidization Example 5

| | | | | | | | | | | | | |
|---|---|---|---|---|---|---|---|---|---|---|---|---|
| Type of reactant ° C. | | | | | | Calcium oxide | | | | | | |
| Reactant packing height mm | | | | | | 200 | | | | | | |
| Temperature ° C. | | | | | | 300 | | | | | | |
| Gas composition | HFC-134a mol % | | | | | 0 | | | | | | |
| ratio | Nitrogen mol % | | | | | 100 | | | | | | |
| Flow rate | HFC-134a mol/min | 0.00 | 0.00 | 0.00 | 0.00 | 0.00 | 0.00 | 0.00 | 0.00 | 0.00 | 0.00 | 0.00 |
| | Nitrogen mol/min | 1.25 | 1.13 | 1.02 | 0.91 | 0.79 | 0.68 | 0.57 | 0.45 | 0.34 | 0.23 | 0.11 |
| Linear velocity cm/s | | 11 | 10 | 9 | 8 | 7 | 6 | 5 | 4 | 3 | 2 | 1 |
| Differential pressure after packing Pa | | 7700 | 7000 | 6300 | 5700 | 5000 | 4300 | 3700 | 3100 | 2500 | 1900 | 1200 |
| Blank differential pressure Pa | | 6500 | 5900 | 5100 | 4500 | 3800 | 3200 | 2600 | 2000 | 1500 | 900 | 400 |
| Calculated differential pressure Pa | | 1200 | 1100 | 1200 | 1200 | 1200 | 1100 | 1100 | 1100 | 1000 | 1000 | 800 |

*Blank Differential Pressure Measurement Example 6 was employed.

The results of the fluidization tests in the above Fluidization Examples 1 to 5 are shown in Table 8. It is found from Table 8 that calcium oxide having an average particle size of 100 μm has favorable flowability, and it can be in a fluidized state by making a gas to flow therethrough at a linear velocity of at least 7 cm/s regardless of the type of the gas and the packing height. Further, it is found that the flowability increases as the temperature increases.

TABLE 8

| | | Fluidization Example 1 | Fluidization Example 2 | Fluidization Example 3 | Fluidization Example 4 | Fluidization Example 5 |
|---|---|---|---|---|---|---|
| Reactant Packing Example | | Packing Example 3 | Packing Example 4 | Packing Example 3 | Packing Example 3 | Packing Example 3 |
| Average particle size of calcium oxide μm | | 100 | 100 | 100 | 100 | 100 |
| Fluidization visualized test apparatus or fluidized bed reaction apparatus | | Fluidized bed reaction apparatus | Fluidized bed reaction apparatus | Fluidized bed reaction apparatus | Fluidized bed reaction apparatus | Fluidized bed reaction apparatus |
| Temperature ° C. | | 25 | 25 | 25 | 200 | 300 |
| Gas composition ratio | HFC-134a mol % | 0 | 0 | 100 | 0 | 0 |
| | Nitrogen mol % | 100 | 100 | 0 | 100 | 100 |
| Linear velocity/ differential pressure plot analysis | Partial fluidization starting velocity | Nil | Nil | Nil | Nil | Nil |
| | Complete fluidization starting velocity | 7 cm/s | 5 cm/s | 6 cm/s | 3 cm/s | 3 cm/s |

Examples 6 to 13

First, in Example 6, the interior of the fluidized bed reactor of the fluidized bed reaction apparatus packed with the solid reactant (calcium oxide having an average particle size of 100 μm) to a height of 300 mm shown in Reactant Packing Example 4 was heated to 300° C. by an electric furnace. Then, a nitrogen gas was made to flow through the fluidized bed reaction apparatus at a flow rate of 0.79 mol/min (linear velocity of 7 cm/s) under normal pressure. From the results of the above Fluidization Examples 1 to 5, it is considered that the layer of calcium oxide was in a completely fluidized state at this linear velocity.

Then, the flow rate of the nitrogen gas was decreased to 0.71 mol/min and at the same time, HFC-134a was started to be made to flow at a flow rate of 0.08 mmol/min. HFC-134a was made to flow and reacted for 2 minutes from the start of the flow of HFC-134a, and then the supply of HFC-134a was terminated and at the same time, the flow rate of the nitrogen gas was changed to 0.79 mol/min, and the reaction in Example 6 was completed. The outlet gas was continuously collected in a PVdF bag for about 10 seconds from 2 minutes after the start of the flow of HFC-134a to the completion of the reaction.

Then, after completion of the reaction in Example 6, without exchanging calcium oxide in the fluidized bed reactor, Examples 7 to 13 were carried out as it was. In Examples 7 to 13, HFC-134a was brought into contact with and reacted with the solid reactant in the same manner as in Example 6 except that the reaction conditions were as identified in Table 9. Further, the composition of the outlet gas collected in the PVdF bag was analyzed by gas chromatography (GC). The analysis results are shown in Table 9 together with the reaction conditions (the nitrogen flow rate before the reaction, the reaction temperature, the HFC-134a flow rate at the time of the reaction, the nitrogen flow rate at the time of the reaction, the composition at the time of the reaction (HFC-134a:nitrogen (molar ratio)), the linear velocity at the time of the reaction, the contact time at the time of the reaction, presence or absence of the fluidized state at the time of the reaction, and the reaction time).

Examples 14 to 18

First, in Example 14, the interior of the fluidized bed reactor of the fluidized bed reaction apparatus packed with the solid reactant (calcium oxide having an average particle size of 100 μm) to a height of 300 mm shown in Reactant Packing Example 4 was heated to 350° C. by an electric furnace. Then, a nitrogen gas was made to flow through the fluidized bed reaction apparatus at a flow rate of 0.73 mmol/min (linear velocity of 7 cm/s) under normal pressure. From the results of the above Fluidization Examples 1 to 5, it is considered that the layer of calcium oxide was in a completely fluidized state at this linear velocity.

Then, the flow of the nitrogen gas was terminated and at the same time, HFC-134a was started to be made to flow at a flow rate of 0.73 mol/min. HFC-134a was made to flow and reacted for 3 minutes from the start of the flow of HFC-134a, and the supply of HFC-134a was terminated and at the same time, the flow rate of the nitrogen gas was changed to 0.73 mol/min, and the reaction in Example 14 was completed. The outlet gas was continuously collected in a PVdF bag for about 10 seconds from 3 minutes after the start of the flow of HFC-134a to the completion of the reaction.

Then, after completion of the reaction in Example 14, without exchanging calcium oxide in the fluidized bed reactor, Examples 15 to 18 were conducted as it was. In Examples 15 to 18, HFC-134a was brought into contact with and reacted with the solid reactant in the same manner as in Example 14 except that the reaction conditions were as identified in Table 10. Further, the composition of the outlet gas collected in the PVdF bag was analyzed by gas chromatography (GC). The analysis results are shown in Table 10 together with the reaction conditions (the nitrogen flow rate before the reaction, the reaction temperature, the HFC-134a flow rate at the time of the reaction, the nitrogen flow rate at the time of the reaction, the composition at the time of the reaction (HFC-134a:nitrogen (molar ratio)), the linear velocity at the time of the reaction, the contact time at the time of the reaction, presence or absence of the fluidized state at the time of the reaction, and the reaction time).

Then, in Examples 6 to 13 and 14 to 18, based on the molar ratio (mol %) calculated from the area ratio of the outlet gas obtained by gas chromatography analysis, the degree of conversion (reactivity) of HFC-134a, the selectivity for HFO-1123 and the selectivity for other gases were obtained as follows. In the following reaction formulae, (HFC-134a) and (HFO-1123) respectively represent the molar ratios (mol %) of (HFC-134a) and (HFO-1123) in the outlet gas.

The results are shown in the lower rows in Table 9 with respect to Examples 6 to 13 and in the lower rows in Table 10 with respect to Examples 14 to 18.

[Degree of Conversion (%) of HFC-134a]

It represents the proportion of components other than HFC-134a among components derived from HFC-134a in the outlet gas. It is calculated from {100−(HFC-134a)}/100× 100(%) in the outlet gas.

[Selectivity (%) for HFO-1123]

It represents the proportion of HFC-134a converted to HFO-1123 based on the entire HFC-134a reacted, represented by %. It is calculated from (HFC-1123)/{100−(HFC-134a)}×100(%) in the outlet gas.

[Selectivity (%) for Other Gases]

It represents the proportion of HFC-134a converted to compounds other than HFO-1123 based on the entire HFC-134a reacted, represented by %. It is calculated from {100−(HFC-134a)−(HFO-1123)}/{100−(HFC-134a)}×100(%) in the outlet gas.

TABLE 9

|  |  | Example 6 | Example 7 | Example 8 | Example 9 | Example 10 | Example 11 | Example 12 | Example 13 |
|---|---|---|---|---|---|---|---|---|---|
| Solid reactant | | Calcium oxide | | | | | | | |
| Reactant packing amount (g) | | 3143 | | | | | | | |
| Reactant packing amount (mol) | | 56.05 | | | | | | | |
| Nitrogen flow rate before reaction (mol/min) | | 0.79 | 0.76 | 0.73 | 0.70 | 0.67 | 0.65 | 0.63 | 0.61 |
| Reaction temperature (° C.) | | 300 | 325 | 350 | 375 | 400 | 425 | 450 | 475 |
| HFC-134a flow rate at the time of reaction (mol/min) | | 0.08 | 0.08 | 0.07 | 0.07 | 0.07 | 0.06 | 0.06 | 0.06 |
| Nitrogen flow rate at the time of reaction (mol/min) | | 0.71 | 0.76 | 0.66 | 0.63 | 0.61 | 0.59 | 0.57 | 0.55 |
| Composition ratio at the time of reaction HFC-134a:N2 (molar ratio) | | 10:90 | 10:90 | 10:90 | 10:90 | 10:90 | 10:90 | 10:90 | 10:90 |
| Linear velocity at the time of reaction (cm/s) | | 7 | 7 | 7 | 7 | 7 | 7 | 7 | 7 |
| Contact time at the time of reaction (s) | | 4.3 | 4.3 | 4.3 | 4.3 | 4.3 | 4.3 | 4.3 | 4.3 |
| Fluidized state at the time of reaction | | Completely fluidized state | | | | | | | |
| Reaction time (min) | | 2 | 2 | 2 | 2 | 2 | 2 | 2 | 2 |
| Structure | Name | Outlet gas composition (other than nitrogen) (mol %) | | | | | | | |
| CF2=CHF | HFO-1123 | 7.64 | 14.23 | 21.22 | 30.91 | 44.09 | 55.59 | 63.57 | 60.70 |
| CF3CH2F | HFC-134a | 92.30 | 85.71 | 78.68 | 68.80 | 55.07 | 41.88 | 29.35 | 22.86 |
| Others | | 0.1 | 0.1 | 0.1 | 0.3 | 0.8 | 2.5 | 7.1 | 16.4 |
| Degree of conversion of HFC-134a (%) | | 7.7 | 14.3 | 21.3 | 31.2 | 44.9 | 58.1 | 70.6 | 77.1 |
| Selectivity for HFO-1123 (%) | | 99.2 | 99.6 | 99.5 | 99.1 | 98.1 | 95.6 | 90.0 | 78.7 |
| Selectivity for other gases (%) | | 0.8 | 0.4 | 0.5 | 0.9 | 1.9 | 4.4 | 10.0 | 21.3 |

TABLE 10

|  | Example 14 | Example 15 | Example 16 | Example 17 | Example 18 |
|---|---|---|---|---|---|
| Solid reactant | Calcium oxide | | | | |
| Reactant packing amount (g) | 3143 | | | | |
| Reactant packing amount (mol) | 56.05 | | | | |
| Nitrogen flow rate before reaction (mol/min) | 0.73 | 0.70 | 0.67 | 0.65 | 0.63 |
| Reaction temperature (° C.) | 350 | 375 | 400 | 425 | 450 |
| HFC-134a flow rate at the time of reaction (mol/min) | 0.73 | 0.70 | 0.67 | 0.65 | 0.63 |

TABLE 10-continued

|  | | Example 14 | Example 15 | Example 16 | Example 17 | Example 18 |
|---|---|---|---|---|---|---|
| Nitrogen flow rate at the time of reaction (mol/min) | | 0.00 | 0.00 | 0.00 | 0.00 | 0.00 |
| Composition ratio at the time of reaction HFC-134a:N2 (molar ratio) | | 100:0 | 100:0 | 100:0 | 100:0 | 100:0 |
| Linear velocity at the time of reaction (cm/s) | | 7 | 7 | 7 | 7 | 7 |
| Contact time at the time of reaction (s) | | 4.3 | 4.3 | 4.3 | 4.3 | 4.3 |
| Fluidized state at the time of reaction | | Completely fluidized state | | | | |
| Reaction time (min) | | 3 | 3 | 3 | 3 | 3 |
| Structure | Name | Outlet gas composition (other than nitrogen) (mol %) | | | | |
| CF2=CHF | HFO-1123 | 4.65 | 6.60 | 10.80 | 17.24 | 29.81 |
| CF3CH2F | HFC-134a | 95.33 | 93.36 | 89.11 | 82.38 | 68.03 |
| Others | | 0.0 | 0.0 | 0.1 | 0.4 | 2.2 |
| Degree of conversion of HFC-134a (%) | | 4.7 | 6.6 | 10.9 | 17.6 | 32.0 |
| Selectivity for HFO-1123 (%) | | 99.5 | 99.5 | 99.2 | 97.9 | 93.3 |
| Selectivity for other gases (%) | | 0.5 | 0.5 | 0.8 | 2.1 | 6.7 |

As evident from Tables 1 and 2, in Examples, the degree of conversion of 134a could be made high and HFO-1123 could be obtained with a sufficiently high selectivity in the same manner as in Comparative Examples 1 to 5 in which HFC-134a was reacted with calcium hydroxide. Further, as evident from Tables 9 and 10, HFO-1123 can be obtained with a high reactivity with a sufficiently high selectivity by reacting HFC-134a with calcium oxide in a fluidized state.

INDUSTRIAL APPLICABILITY

The method for producing HFO-1123 of the present invention is a novel production method, by which HFO-1123 can be produced with a sufficiently high selectivity. Further, problems such as clogging of a reactor, an increase in the load of the moisture removal process due to formation of a large amount of moisture as a by-product and a decrease in the yield of HFO-1123 will not arise, and thus the production method is suitably applicable to production of HFO-1123.

REFERENCE SYMBOLS

1: Fixed bed reaction apparatus, 2: fixed bed reactor, 3: solid reactant layer, 4: preheating mixer, 5: material gas supply line, 6: HFC-134a supply line, 7: diluent gas supply line, 8: heating means, 9: outlet line, 10: hydrogen fluoride trapping tube, 11: sampling bag, 12: fluidized bed reaction apparatus, 13: fluidized bed reactor, 14: gas mixture supply line, 15: differential pressure gauge.

What is claimed is:
1. A method for producing trifluoroethylene, the method comprising:
contacting a material gas comprising 1,1,1,2-tetrafluoroethane and an inert gas with calcium oxide at a temperature of 200 to 500° C. in a reactor,
wherein a molar ratio of 1,1,1,2-tetrafluoroethane to the inert gas (1,1,1,2-tetrafluoroethane:inert gas) at the contacting is from 20:80 to 100:0, and wherein the inert gas is nitrogen.

2. The method according to claim 1, wherein the material gas is in a gaseous phase and calcium oxide is in a solid phase.

3. The method according to claim 1, wherein said contacting occurs at a temperature of 300 to 450° C.

4. The method according to claim 1, wherein said contacting occurs at a pressure of from 0 to 2 MPa by gauge pressure.

5. The method according to claim 2, wherein a specific surface area of calcium oxide is from 0.1 to 500 m$^2$/g.

6. The method according to claim 1, wherein the material gas is introduced to a fixed bed reactor packed with calcium oxide.

7. The method according to claim 6, wherein a contact time of 1,1,1,2-tetrafluoroethane and calcium oxide in the fixed bed reactor is from 0.5 to 20 seconds.

8. The method according to claim 1, wherein the material gas is introduced to a fluidized bed reactor packed with calcium oxide.

9. The method according to claim 8, wherein a contact time of 1,1,1,2-tetrafluoroethane and calcium oxide in the fluidized bed reactor is from 0.1 to 20 seconds.

10. The method according to claim 1, wherein 1,1,1,2-tetrafluoroethane is preheated to a temperature of 80 to 450° C. before 1,1,1,2-tetrafluoroethane is introduced into the reactor.

11. The method according to claim 5, wherein the specific surface area of calcium oxide is from 1 to 200 m$^2$/g.

* * * * *